United States Patent
Peters et al.

(10) Patent No.: US 7,678,788 B2
(45) Date of Patent: Mar. 16, 2010

(54) DIAZABICYCLIC ARYL DERIVATIVES

(75) Inventors: Dan Peters, Malmoe (SE); Gunnar M. Olsen, Ballerup (DK); Elsebet Østergaard Nielsen, Ballerup (DK); Tino Dyhring Jørgensen, Ballerup (DK); Philip K. Ahring, Ballerup (DK)

(73) Assignee: Neurosearch A/S, Ballerup (DK)

( * ) Notice: Subject to any disclaimer, the term of this patent is extended or adjusted under 35 U.S.C. 154(b) by 1005 days.

(21) Appl. No.: 10/547,157

(22) PCT Filed: Feb. 4, 2004

(86) PCT No.: PCT/EP2004/050079

§ 371 (c)(1),
(2), (4) Date: Aug. 26, 2005

(87) PCT Pub. No.: WO2004/076453

PCT Pub. Date: Sep. 10, 2004

(65) Prior Publication Data

US 2006/0148789 A1   Jul. 6, 2006

Related U.S. Application Data

(60) Provisional application No. 60/449,871, filed on Feb. 27, 2003, provisional application No. 60/482,022, filed on Jun. 25, 2003.

(30) Foreign Application Priority Data

Feb. 27, 2003   (DK) ............................... 2003 00310
Jun. 24, 2003   (DK) ............................... 2003 00940

(51) Int. Cl.
*A61P 25/00*   (2006.01)
*A61K 31/55*   (2006.01)
*C07D 471/08*   (2006.01)

(52) U.S. Cl. ..................................... 514/221; 540/556
(58) Field of Classification Search ................. 514/221; 540/556
See application file for complete search history.

(56) References Cited

U.S. PATENT DOCUMENTS

| | | | |
|---|---|---|---|
| 6,552,012 B2 | 4/2003 | Peters et al. | |
| 2003/0119837 A1 | 6/2003 | O'Donnell | |
| 2003/0119840 A1 | 6/2003 | LeClerc et al. | |
| 2004/0266757 A1 | 12/2004 | Galli et al. | |
| 2005/0020599 A1 | 1/2005 | Galli et al. | |
| 2005/0239774 A1* | 10/2005 | Ernst et al. | 514/221 |
| 2006/0052368 A1* | 3/2006 | Ernst et al. | 514/221 |

FOREIGN PATENT DOCUMENTS

| | | |
|---|---|---|
| EP | 1 231 212 A | 8/2002 |
| FR | 2 832 712 A | 5/2003 |
| FR | 2 832 713 A | 5/2003 |
| WO | WO-00/58311 A | 10/2000 |
| WO | WO-2004/016616 A1 | 2/2004 |
| WO | WO-2004/029053 A1 | 4/2004 |
| WO | WO-2004/004396 A | 5/2004 |

* cited by examiner

*Primary Examiner*—Brenda L Coleman
(74) *Attorney, Agent, or Firm*—Birch, Stewart, Kolasch & Birch, LLP.

(57) ABSTRACT

This invention relates to novel diazabicyclic aryl derivatives which are found to be cholinergic ligands at the nicotinic acetylcholine receptors. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

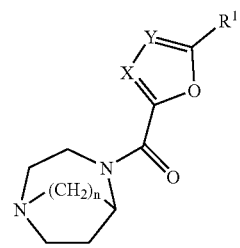

(I)

4 Claims, No Drawings

DIAZABICYCLIC ARYL DERIVATIVES

This application is the National Phase of PCT application PCT/EP2004/050079, filed Feb. 4, 2004 and claims priority under 35 U.S.C. 119(e) on U.S. Provisional Application Nos. 60/449,871 and 60/482,022 filed on Feb. 27, 2003 and Jun. 25, 2003, respectively and under 35 U.S.C. 119(a) on Patent Application No(s). PA 2003 00310 and PA 2003 00940 filed in Denmark on Feb. 27, 2003 and Jun. 24, 2003, respectively, all of which are hereby incorporated by reference.

TECHNICAL FIELD

This invention relates to novel diazabicyclic aryl derivatives, which are found to be cholinergic ligands at the nicotinic acetylcholine receptors. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neurodegeneration, diseases or disorders related to inflammation, pain, and withdrawal symptoms caused by the termination of abuse of chemical substances.

BACKGROUND ART

The endogenous cholinergic neurotransmitter, acetylcholine, exert its biological effect via two types of cholinergic receptors, the muscarinic Acetyl Choline Receptors (mAChR) and the nicotinic Acetyl Choline Receptors (nAChR).

As it is well established that muscarinic acetylcholine receptors dominate quantitatively over nicotinic acetylcholine receptors in the brain area important to memory and cognition, and much research aimed at the development of agents for the treatment of memory related disorders have focused on the synthesis of muscarinic acetylcholine receptor modulators.

Recently, however, an interest in the development of nAChR modulators has emerged. Several diseases are associated with degeneration of the cholinergic system i.e. senile dementia of the Alzheimer type, vascular dementia and cognitive impairment due to the organic brain damage disease related directly to alcoholism.

WO 00/58311 discloses 1,4-diazabicyclo[3.2.2]nonane-4-carboxylates and carboxamide derivatives useful as inhibitors of the nicotinic α7 receptor subtype. Other 1,4-diazabicyclo[3.2.2]nonane-4-methanone derivatives are not disclosed.

SUMMARY OF THE INVENTION

The present invention is devoted to the provision novel modulators of the nicotnic receptors, which modulators are useful for the treatment of diseases or disorders related to the chollnergic receptors, and in particular the nicotinic acetylcholine α7 receptor subtype.

The compounds of the invention may also be useful as diagnostic tools or monitoring agents in various diagnostic methods, and in particular for in vivo receptor imaging (neuroimaging), and they may be used in labelled or unlabelled form.

In its first aspect the invention provides diazabicyclic aryl derivatives of Formula I

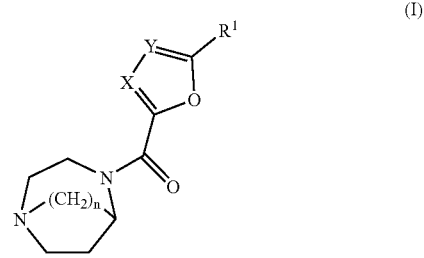

any of its enantiomers or any mixture of its enantiomers, or a prodrug, or a pharmaceutically-acceptable addition salt thereof, wherein n is 1, 2 or 3; and X and Y, independently of one another, represents $CR^2$, $CR^3$ and/or N, wherein $R^2$ and $R^3$, independently of one another, represent hydrogen, alkyl, cycloalkyl, cycloalkyl-alkyl, hydroxy, alkoxy, cycloalkoxy, cyanoalkyl, halo, haloalkyl, haloalkoxy, cyano, amino, nitro, aryl, aryloxy, aryl-alkyl, heteroaryl and/or heteroaryloxy, which aryl, aryloxy, aryl-alkyl, heteroaryl and heteroaryloxy may optionally be substituted one or two times with halo, haloalkyl, haloalkoxy, cyano, amino, nitro and/or a group of the formula R'CONH—, wherein R' represents hydrogen or alkyl; and $R^1$ represents hydrogen, alkyl, cycloalkyl, cycloalkyl-alkyl, hydroxy, alkoxy, cycloalkoxy, cyanoalkyl, halo, haloalkyl, haloalkoxy, cyano, amino, nitro, aryl or heteroaryl, which aryl or heteroaryl may optionally be substituted one or two times with alkyl, halo, haloalkyl, alkoxy, haloalkoxy, cyano, amino, nitro and/or a group of the formula R'CONH—, $R'SO_2NH$— or $(R'SO_2)_2N$—, wherein R' represents hydrogen, alkyl, cycloalkyl, haloalkyl, alkenyl, phenyl or benzyl; or a group of formula aryl-alkyl-, aryl-Z-(alkyl)$_m$-, aryl-C≡C—, heteroaryl-Z-(alkyl)$_m$- or heteroaryl-C≡C—, wherein m is 0 or 1; and Z represents O or S; and wherein the aryl and heteroaryl may optionally be substituted one or two times with alkyl, halo, haloalkyl, hydroxy, alkoxy, haloalkoxy, cyano, amino, nitro and/or a group of the formula R'CONH—, $R'SO_2NH$— or $(R'SO_2)_2N$—, wherein R' represents hydrogen or alkyl; or $R^1$ and $R^2$, or $R^1$ and $R^3$, together with the carbon atoms to which they are bound, form a benzo-fused aromatic carbocyclic ring, which benzo-fused aromatic carbocyclic ring may optionally be substituted one or two times with alkyl, cycloalkyl, cycloalkyl-alkyl, hydroxy, alkoxy, cycloalkoxy, cyanoalkyl, halo, haloalkyl, haloalkoxy, cyano, amino, nitro and/or a group of the formula R'CONH—, wherein R' represents hydrogen or alkyl.

In a second aspect the invention provides pharmaceutical compositions comprising a therapeutically effective amount of the diazabicyclic aryl derivative of the invention, or a pharmaceutically-acceptable addition salt thereof, together with at least one pharmaceutically-acceptable carrier or diluent.

Viewed from another aspect the invention relates to the use of the diazabicyclic aryl derivative of the invention, or a pharmaceutically-acceptable addition salt thereof, for the manufacture of pharmaceutical compositions/medicaments for the treatment, prevention or alleviation of a disease or a disorder or a condition of a mammal, including a human, which disease, disorder or condition is responsive to modulation of cholinergic receptors.

In yet another aspect the invention provides a method for treatment, prevention or alleviation of diseases, disorders or conditions of a living animal body, including a human, which disorder, disease or condition is responsive to modulation of cholinergic receptors, and which method comprises the step of administering to such a living animal body in need thereof a therapeutically effective amount of the diazabicyclic aryl derivative of the invention.

Other objects of the invention will be apparent to the person skilled in the art from the following detailed description and examples.

DETAILED DISCLOSURE OF THE INVENTION

Diazabicyclic Aryl Derivatives

In a first aspect the invention provides a diazabicyclic aryl derivative of Formula I

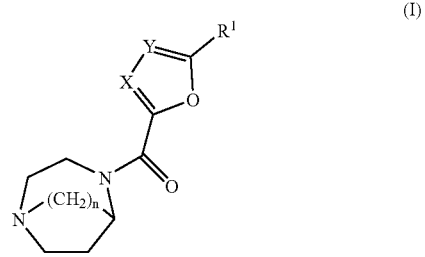

any of its enantiomers or any mixture of its enantiomers, or a prodrug, or a pharmaceutically-acceptable addition salt thereof, wherein n is 1, 2 or 3; and X and Y, independently of one another, represents $CR^2$, $CR^3$ and/or N, wherein $R^2$ and $R^3$, independently of one another, represent hydrogen, alkyl, cycloalkyl, cycloalkyl-alkyl, hydroxy, alkoxy, cycloalkoxy, cyanoalkyl, halo, haloalkyl, haloalkoxy, cyano, amino, nitro, aryl, aryloxy, aryl-alkyl, heteroaryl and/or heteroaryloxy, which aryl, aryloxy, aryl-alkyl, heteroaryl and heteroaryloxy may optionally be substituted one or two times with halo, haloalkyl, haloalkoxy, cyano, amino, nitro and/or a group of the formula R'CONH—, wherein R' represents hydrogen or alkyl; and $R^1$ represents hydrogen, alkyl, cycloalkyl, cycloalkyl-alkyl, hydroxy, alkoxy, cycloalkoxy, cyanoalkyl, halo, haloalkyl, haloalkoxy, cyano, amino, nitro, aryl or heteroaryl, which aryl or heteroaryl may optionally be substituted one or two times with alkyl, halo, haloalkyl, alkoxy, haloalkoxy, cyano, amino, nitro and/or a group of the formula R'CONH—, R'SO$_2$NH— or (R'SO$_2$)$_2$N—, wherein R' represents hydrogen, alkyl, cycloalkyl, haloalkyl, alkenyl, phenyl or benzyl; or a group of formula aryl-alkyl-, aryl-Z-(alkyl)$_m$-, aryl-C≡C—, heteroaryl-Z-(alkyl)$_m$- or heteroaryl-C≡C—, wherein m is 0 or 1; and Z represents O or S; and wherein the aryl and heteroaryl may optionally be substituted one or two times with alkyl, halo, haloalkyl, hydroxy, alkoxy, haloalkoxy, cyano, amino, nitro and/or a group of the formula R'CONH—, R'SO$_2$NH— or (R'SO$_2$)$_2$N—, wherein R' represents hydrogen or alkyl; or $R^1$ and $R^2$, or $R^1$ and $R^3$, together with the carbon atoms to which they are bound, form a benzo-fused aromatic carbocyclic ring, which benzo-fused aromatic carbocyclic ring may optionally be substituted one or two times with alkyl, cycloalkyl, cycloalkyl-alkyl, hydroxy, alkoxy, cycloalkoxy, cyanoalkyl, halo, haloalkyl, haloalkoxy, cyano, amino, nitro and/or a group of the formula R'CONH—, wherein R' represents hydrogen or alkyl.

In a preferred embodiment the invention provides a diazabicyclic aryl derivative of Formula I, wherein X represents $CR^3$ or N, wherein $R^3$ represents hydrogen, alkyl, cycloalkyl, cycloalkyl-alkyl, alkoxy, cycloalkoxy, cyanoalkyl, halogen, $CF_3$, $OCF_3$, CN, amino, nitro, aryl, aryloxy, heteroaryl or heteroaryloxy;

$R^1$ and $R^2$, independently of each other, represent hydrogen, alkyl, cycloalkyl, cycloalkyl-alkyl, alkoxy, cycloalkoxy, cyanoalkyl, halogen, $CF_3$, $OCF_3$, CN, amino, nitro, aryl, aryloxy, heteroaryl or heteroaryloxy; or $R^1$ and $R^2$, together with the carbon atoms to which they are bound, form a benzo-fused aromatic carbocyclic ring.

In another preferred embodiment the invention provides a diazabicyclic aryl derivative of Formula I, wherein X and Y, independently of one another, represents $CR^2$ or N, wherein $R^2$ represents hydrogen, alkyl, cycloalkyl, cycloalkyl-alkyl, alkoxy, cycloalkoxy, cyanoalkyl, halo, haloalkyl, haloalkoxy, cyano, amino, nitro, aryl, aryloxy, heteroaryl or heteroaryloxy, which aryl, aryloxy, heteroaryl or heteroaryloxy may optionally be substituted one or two times with halo, haloalkyl, haloalkoxy, cyano, amino, nitro, and/or a group of the formula R'CONH—, wherein R' represents hydrogen or alkyl; and $R^1$ represent hydrogen, alkyl, cycloalkyl, cycloalkyl-alkyl, alkoxy, cycloalkoxy, cyanoalkyl, halo, haloalkyl, haloalkoxy, cyano, amino, nitro, aryl, aryloxy, heteroaryl or heteroaryloxy, which aryl, aryloxy, heteroaryl or heteroaryloxy may optionally be substituted one or two times with halo, haloalkyl, haloalkoxy, cyano, amino, nitro, and/or a group of the formula R'CONH—, wherein R' represents hydrogen or alkyl; or $R^1$ and $R^2$, together with the carbon atoms to which they are bound, form a benzo-fused aromatic carbocyclic ring, which benzo-fused aromatic carbocyclic ring may optionalle be substituted one or two times with alkyl, cycloalkyl, cycloalkyl-alkyl, alkoxy, cycloalkoxy, cyanoalkyl, halo, haloalkyl, haloalkoxy, cyano, amino, nitro, and/or a group of the formula R'CONH—, wherein R' represents hydrogen or alkyl.

In a more preferred embodiment aryl is selected from the group consisting of phenyl, indenyl and naphthyl; and heteroaryl represents an aromatic 5- and 6-membered monocyclic heterocyclic group selected from the group consisting of furanyl, in particular furan-2- or 3-yl; thienyl, in particular thien-2- or 3-yl; pyrrolyl (azolyl), in particular pyrrol-2- or 3-yl; oxazolyl, in particular oxazol-2-, 4- or 5-yl; imidazolyl, in particular imidazol-2- or 4-yl; pyrazolyl, in particular pyrazol-1-, 3- or 4-yl; isoxazolyl, in particular isoxazol-3-, 4- or 5-yl; thiazolyl, in particular thiazol-2-, 4- or 5-yl, thiadiazolyl, in particular 1,3,4-thiadiazol-2-yl, pyridyl, in particular pyrid-2-, 3- or 4-yl; pyridazinyl, in particular pyridazin-3- or 4-yl; pyrimidinyl, in particular pyrimidin-2-, 4- or 5-yl; and pyrazinyl, in particular pyrazin-2- or 3-yl; or an aromatic bicyclic heterocyclic group the group consisting of indolyl, in particular indol-2-, 3-, 5- or 6-yl, benzo[b]furanyl, in particular benzofuran-2-, 5- or 6-yl; benzo[b]thienyl, in particular benzothien-2-, 5- or 6-yl; benzoimidazolyl, in particular benzoimidazol-2-, 5- or 6-yl; quinolinyl, in particular quinolin-2-, 3-, 6- or 7-yl; isoquinolinyl, in particular isoquinolin-3-, 6- or 7-yl; and cinnolinyl, in particular cinnolin-6- or 7-yl.

In a even more preferred embodiment aryl represents phenyl; aryl-alkyl represents benzyl; and heteroaryl represents furanyl, in particular furan-2- or 3-yl; imidazolyl, in particular imidazol-2- or 4-yl; isoxazolyl, in particular isoxazol-3-, 4- or 5-yl; thiazolyl, in particular thiazol-2-, 4- or 5-yl, thiadiazolyl, in particular 1,3,4-thiadiazol-2-yl, pyridyl, in particular pyrid-2-, 3- or 4-yl; or indolyl, in particular indol-2-, 3-, 5- or 6-yl.

In a third preferred embodiment the invention provides a diazabicyclic aryl derivative of Formula I, Ia, Ib, II or III, wherein n is 1, 2 or 3. In a more preferred embodiment the diazabicyclic aryl of the invention is a diazabicyclic aryl derivative of Formula I, Ia, Ib, II or III, wherein n is 2.

In a fourth preferred embodiment the invention provides a diazabicyclic aryl derivative of Formula I, wherein at least one of X and Y represents N; and the other of X and Y represent $CR^2$; and n, $R^1$ and $R^2$ are as defined above.

In a fifth preferred embodiment the invention provides a diazabicyclic aryl derivative of Formula Ia or Ib,

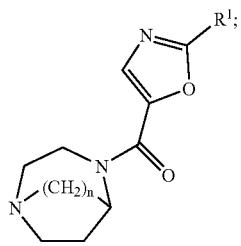

(Ia)

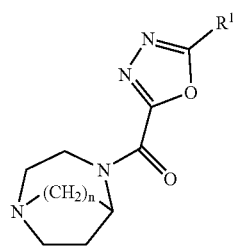

(Ib)

wherein, n and R1 are as defined above.

In a sixth preferred embodiment the invention provides a diazabicyclic aryl derivative of Formula Ic or Id,

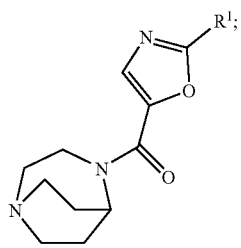

(Ic)

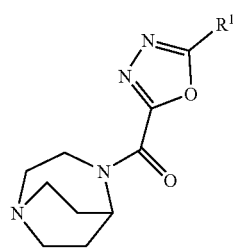

(Id)

wherein, R1 is as defined above.

In a most preferred embodiment the diazabicyclic aryl derivative of the invention is (1,4-Diaza-bicyclo[3.2.2]non-4-yl)-oxazolyl-5-yl-methanone;

(1,4-Diaza-bicyclo[3.2.2]non-4-yl)-(5-phenyl-oxazol-5-yl)-methanone; or (1,4-Diaza-bicyclo[3.2.2]non-4-yl)-5-phenyl-1,3,4-oxadiazol-2-yl-methanone;

an enantiomers or a mixture of its enantiomers, or a pharmaceutically-acceptable addition salt thereof.

In a seventh preferred embodiment the invention provides a diazabicyclic aryl derivative of Formula I, wherein one or two of $R^2$ and $R^3$, independently of one another, represent hydrogen and/or halo; and $R^1$ and the remainder of $R^2$ and $R^3$, independently of one another, represent hydrogen, alkyl, cycloalkyl, cycloalkyl-alkyl, hydroxy, alkoxy, halo, $CF_3$, $OCF_3$, CN, nitro, phenyl, 2-nitro-phenyl, 2-nitro-4-methyl-phenyl, 3-nitro-phenyl, 4-nitro-phenyl, 3-trifluoromethyl-phenyl, 4-trifluoromethyl-phenyl, 2-halo-5-trifluoromethyl-phenyl, 2-amino-phenyl, 2-amino-4-methyl-phenyl, 3-amino-phenyl, 4-amino-phenyl, 2-amino-4-methyl-phenyl, 4-halo-phenyl, 4-formylamino-phenyl, 2-acetylamino-phenyl, 3-acetylamino-phenyl, 4-acetylamino-phenyl, N-3-phenyl-acetamide, N-4-phenyl-acetamide, N-4-phenyl-propionamide, N-4-phenyl-isobutyramide, N-4-phenyl-acrylamide, N-4-phenyl-benzamide, 4-(N,N-dimethyl-sulfonyl-amino)-phenyl, N-4-phenyl-2,2,2-trifluoro-acetamide trifluoro acetic acid, 4-phenyl-cyclopropanecarboxylic acid amide, 4-phenyloxy, 3,5-dihalo-phenyloxy, phenyl-ethynyl, 2-pyridyl, 3-pyridyl, 4-pyridyl, 2-pyridyl-thiomethyl and/or 5-trifluoromethyl-2-pyridyl-thiomethyl.

In an eighth preferred embodiment the invention provides a diazabicyclic aryl derivative of Formula I, wherein one of $R^1$ and $R^2$ represents phenyl or naphthyl; and the other of $R^1$ and $R^2$ represents hydrogen.

In a ninth preferred embodiment the invention provides a diazabicyclic aryl derivative of Formula I, wherein both of X and Y represent $CR^2$, $CR^3$ or N, wherein $R^2$ and $R^3$, independently of one another, represent hydrogen, alkyl, cycloalkyl, cycloalkyl-alkyl, hydroxy, alkoxy, cycloalkoxy, cyanoalkyl, halo, haloalkyl, haloalkoxy, cyano, amino, nitro, aryl, aryloxy, heteroaryl and/or heteroaryloxy, which aryl, aryloxy, heteroaryl and heteroaryloxy may optionally be substituted one or two times with halo, haloalkyl, haloalkoxy, cyano, amino, nitro and/or a group of the formula R'CONH—, wherein R' represents hydrogen or alkyl; or X represents N or $CR^2$, wherein $R^2$ represents hydrogen, alkyl, cycloalkyl, cycloalkyl-alkyl, hydroxy, alkoxy, cycloalkoxy, cyanoalkyl, halo, haloalkyl, haloalkoxy, cyano, amino, nitro, aryl, aryloxy, heteroaryl or heteroaryloxy, which aryl, aryloxy, heteroaryl or heteroaryloxy may optionally be substituted one or two times with halo, haloalkyl, haloalkoxy, cyano, amino, nitro and/or a group of the formula R'CONH—, wherein R' represents hydrogen or alkyl; and Y represents N or $CR^3$, wherein $R^3$ together with $R^1$, and together with the carbon atoms to which they are bound, form a benzo-fused aromatic carbocyclic ring, which benzo-fused aromatic carbocyclic ring may optionally be substituted one or two times with alkyl, cycloalkyl, cycloalkyl-alkyl, hydroxy, alkoxy, cycloalkoxy, cyanoalkyl, halo, haloalkyl, haloalkoxy, cyano, amino, nitro and/or a group of the formula R'CONH—, wherein R' represents hydrogen or alkyl.

In a tenth preferred embodiment the invention provides a diazabicyclic aryl derivative of Formula II,

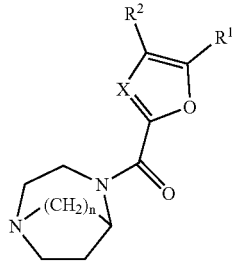

(II)

any of its enantiomers or any mixture of its enantiomers, or a prodrug, or a pharmaceutically-acceptable addition salt thereof, wherein n is 1, 2 or 3; and X represents $CR^4$ or N, wherein $R^4$ represents hydrogen, alkyl, cycloalkyl, cycloalkyl-alkyl, hydroxy, alkoxy, cycloalkoxy, cyanoalkyl, halo, haloalkyl, haloalkoxy, cyano, amino, nitro, aryl, aryloxy, heteroaryl or heteroaryloxy, which aryl, aryloxy, heteroaryl or heteroaryloxy may optionally be substituted one or two times with halo, haloalkyl, haloalkoxy, cyano, amino, nitro and/or a group of the formula R'CONH—, wherein R' represents hydrogen or alkyl;

$R^1$ and $R^2$, independently of each other, represent hydrogen, alkyl, cycloalkyl, cycloalkyl-alkyl, hydroxy, alkoxy, cycloalkoxy, cyanoalkyl, halo, haloalkyl, haloalkoxy, cyano, amino, nitro, phenyl, phenyloxy, heteroaryl and/or heteroaryloxy, which phenyl, phenyloxy, heteroaryl and heteroaryloxy may optionally be substituted one or two times with alkyl, halo, haloalkyl, haloalkoxy, cyano, amino, nitro, a group of the formula R'CONH—, R'SO$_2$NH— and/or (R'SO$_2$)$_2$N—, wherein R' represents hydrogen, alkyl, cycloalkyl, haloalkyl, alkenyl, phenyl or benzyl;

wherein R' represents hydrogen or alkyl; or $R^1$ and $R^2$, together with the carbon atoms to which they are bound, form a benzo-fused aromatic benzene ring, which benzene ring may optionally be substituted one or two times with alkyl, cycloalkyl, cycloalkyl-alkyl, hydroxy, alkoxy, cycloalkoxy, cyanoalkyl, halo, haloalkyl, haloalkoxy, cyano, amino, nitro, aryl, aryloxy, heteroaryl or heteroaryloxy, which aryl, aryloxy, heteroaryl or heteroaryloxy may optionally be substituted one or two times with halo, haloalkyl, haloalkoxy, cyano, amino, nitro and/or a group of the formula R'CONH—, wherein R' represents hydrogen or alkyl.

In a more preferred embodiment the diazabicyclic aryl derivative of the invention is a diazabicyclic aryl derivative of Formula II, wherein $R^1$ represents hydrogen, alkyl, cycloalkyl, cycloalkyl-alkyl, alkoxy, halo, $CF_3$, $OCF_3$, CN, nitro, phenyl, 2-nitro-phenyl, 2-nitro-4-methyl-phenyl, 3-nitro-phenyl, 4-nitro-phenyl, 3-trifluoromethyl-phenyl, 4-trifluoromethyl-phenyl, 2-halo-5-trifluoromethyl-phenyl, 2-amino-phenyl, 2-amino-4-methyl-phenyl, 3-amino-phenyl, 4-amino-phenyl, 2-amino-4-methyl-phenyl, 4-halo-phenyl, 4-formylamino-phenyl, 2-acetylamino-phenyl, 3-acetylamino-phenyl, 4-acetylamino-phenyl, N-3-phenyl-acetamide, N-4-phenyl-acetamide, N-4-phenyl-propionamide, N-4-phenyl-isobutyramide, N-4-phenyl-acrylamide, N-4-phenyl-benzamide, 4-(N,N-dimethyl-sulfonyl-amino)-phenyl, N-4-phenyl-2,2,2-trifluoro-acetamide trifluoro acetic acid, 4-phenyl-cyclopropanecarboxylic acid amide, 4-phenyloxy, 3,5-dihalo-phenyloxy, phenyl-ethynyl, 2-pyridyl, 3-pyridyl, 4-pyridyl, 2-pyridyl-thiomethyl or 5-trifluoromethyl-2-pyridyl-thiomethyl;

$R^2$ represents hydrogen or halo; and $R^4$ represents hydrogen, alkyl or halo.

In an eleventh preferred embodiment the invention provides a diazabicyclic aryl derivative of Formula III,

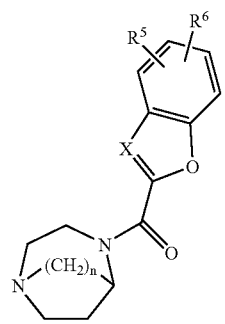

(III)

any of its enantiomers or any mixture of its enantiomers, or a prodrug, or a pharmaceutically-acceptable addition salt thereof, wherein n is 1, 2 or 3; and X represents $CR^4$ or N, wherein $R^4$ represents hydrogen, alkyl, cycloalkyl, cycloalkyl-alkyl, hydroxy, alkoxy, cycloalkoxy, cyanoalkyl, halo, haloalkyl, haloalkoxy, cyano, amino, nitro, aryl, aryloxy, heteroaryl or heteroaryloxy;

$R^5$ and $R^6$, independently of each other, represent hydrogen, alkyl, cycloalkyl, cycloalkyl-alkyl, hydroxy, alkoxy, cycloalkoxy, cyanoalkyl, halo, haloalkyl, haloalkoxy, cyano, amino, nitro, aryl, aryloxy, heteroaryl or heteroaryloxy.

In a more preferred embodiment the diazabicyclic aryl derivative of the invention is a diazabicyclic aryl derivative of Formula III, wherein $R^4$ represents hydrogen or alkyl; $R^5$ represents hydrogen, alkyl or alkoxy; and $R^6$ represents hydrogen, alkyl or alkoxy.

In a most preferred embodiment the diazabicyclic aryl derivative of the invention is (1,4-Diaza-bicyclo[3.2.2]non-4-yl)-8-methoxy-benzofuran-2-yl-methanone;

(1,4-Diaza-bicyclo[3.2.2]non-4-yl)-benzofuran-2-yl-methanone; or (1,4-Diaza-bicyclo[3.2.2]non-4-yl)-3-methyl-benzofuran-2-yl-methanone;

(1,4-Diaza-bicyclo[3.2.2]non-4-yl)-benzooxazol-2-yl-methanone;

an enantiomers or a mixture of its enantiomers, or a pharmaceutically-acceptable addition salt thereof.

In a twelfth preferred embodiment the invention provides a diazabicyclic aryl derivative of Formula I, Ia, Ib or II, wherein $R^1$ represents a group of formula -(alkyl)$_m$-Z-aryl, -(alkyl)$_m$-Z-heteroaryl or —C≡C-aryl, wherein m is 0 or 1; and Z represents O or S; and wherein the aryl and heteroaryl may optionally be substituted one or two times with alkyl, halo, haloalkyl, alkoxy, haloalkoxy, cyano, amino, nitro and/or a group of the formula R'CONH—, R'SO$_2$NH— or (R'SO$_2$)$_2$N—, wherein R' represents hydrogen or alkyl.

In a thirteenth preferred embodiment the invention provides a diazabicyclic aryl derivative of Formula I, Ia, Ib or II, wherein $R^1$ represents a group of formula —CH$_2$-Z-phenyl, —CH$_2$-Z-pyridyl or —C≡C-phenyl, wherein m is 0 or 1; and Z represents O or S; and wherein the phenyl and pyridyl group may optionally be substituted one or two times with alkyl, halo, haloalkyl, alkoxy, haloalkoxy, cyano, amino, nitro and/or a group of the formula R'CONH—, R'SO$_2$NH— or (R'SO$_2$)$_2$N—, wherein R' represents hydrogen or alkyl.

In a most preferred embodiment the diazabicyclic aryl derivative of the invention is
(1,4-Diaza-bicyclo[3.2.2]non-4-yl)-5-(3,5-dichlorophenoxy)-furan-2-yl-methanone;
(1,4-Diaza-bicyclo[3.2.2]non-4-yl)-5-[5-(trifluoromethyl-2-pyridyl)-thiomethyl]-furan-2-yl-methanone; or
(1,4-Diaza-bicyclo[3.2.2]non-4-yl)-5-phenylethynyl-furan-2-yl-methanone;
an enantiomers or a mixture of its enantiomers, or a pharmaceutically-acceptable addition salt thereof.

In a fourteenth preferred embodiment the invention provides a diazabicyclic aryl derivative of Formula I or II, wherein R$^1$ represents hydrogen, alkyl, cycloalkyl, cycloalkyl-alkyl, alkoxy, halo, CF$_3$, OCF$_3$, CN, nitro, phenyl, 2-nitro-phenyl, 2-nitro-4-methyl-phenyl, 3-nitro-phenyl, 4-nitro-phenyl, 3-trifluoromethyl-phenyl, 4-trifluoromethyl-phenyl, 2-halo-5-trifluoromethyl-phenyl, 2-amino-phenyl, 2-amino-4-methyl-phenyl, 3-amino-phenyl, 4-amino-phenyl, 2-amino-4-methyl-phenyl, 4-halo-phenyl, 4-formylamino-phenyl, 2-acetylamino-phenyl, 3-acetylamino-phenyl, 4-acetylamino-phenyl, N-3-phenyl-acetamide, N-4-phenyl-acetamide, N-4-phenyl-propionamide, N-4-phenyl-isobutyramide, N-4-phenyl-acrylamide, N-4-phenyl-benzamide, 4-(N,N-dimethyl-sulfonyl-amino)-phenyl, N-4-phenyl-2,2,2-trifluoro-acetamide trifluoro acetic acid, 4-phenyl-cyclopropanecarboxylic acid amide, 4-phenyloxy, 3,5-dihalo-phenyloxy, phenyl-ethynyl, 2-pyridyl, 3-pyridyl, 4-pyridyl, 2-pyridyl-thiomethyl or 5-trifluoromethyl-2-pyridyl-thiomethyl;

R$^2$ represents hydrogen, alkyl or halo; and
R$^3$ represents hydrogen, alkyl or halo.

In a most preferred embodiment the diazabicyclic aryl derivative of the invention is
(1,4-Diaza-bicyclo[3.2.2]non-4-yl)-furan-2-yl-methanone;
(1,4-Diaza-bicyclo[3.2.2]non-4-yl)-5-bromo-furan-2-yl-methanone;
(1,4-Diaza-bicyclo[3.2.2]non-4-yl)-5-nitro-furan-2-yl-methanone;
(1,4-Diaza-bicyclo[3.2.2]non-4-yl)-(5-phenyl-furan-2-yl)-methanone;
(1,4-Diaza-bicyclo[3.2.2]non-4-yl)-5-(4-nitrophenyl)-furan-2-yl-methanone;
(1,4-Diaza-bicyclo[3.2.2]non-4-yl)-5-(3-trifluoromethylphenyl)-furan-2-yl-methanone;
(1,4-Diaza-bicyclo[3.2.2]non-4-yl)-5-(4-aminophenyl)-furan-2-yl-methanone;
(1,4-Diaza-bicyclo[3.2.2]non-4-yl)-5-(4-chlorophenyl)-furan-2-yl-methanone;
(1,4-Diaza-bicyclo[3.2.2]non-4-yl)-5-(2-nitrophenyl)-furan-2-yl-methanone;
(1,4-Diaza-bicyclo[3.2.2]non-4-yl)-5-(3-nitrophenyl)-furan-2-yl-methanone;
(1,4-Diaza-bicyclo[3.2.2]non-4-yl)-5-(4-acetylaminophenyl)-furan-2-yl-methanone;
(1,4-Diaza-bicyclo[3.2.2]non-4-yl)-5-(2-aminophenyl)-furan-2-yl-methanone;
(1,4-Diaza-bicyclo[3.2.2]non-4-yl)-5-(3-aminophenyl)-furan-2-yl-methanone;
(1,4-Diaza-bicyclo[3.2.2]non-4-yl)-5-(2-acetylaminophenyl)-furan-2-yl-methanone
(1,4-Diaza-bicyclo[3.2.2]non-4-yl)-5-(3-acetylaminophenyl)-furan-2-yl-methanone;
(1,4-Diaza-bicyclo[3.2.2]non-4-yl)-3-methyl-furan-2-yl-methanone;
(1,4-Diaza-bicyclo[3.2.2]non 4-yl)-4,5-dibromo-furan-2-yl-methanone;
(1,4-Diaza-bicyclo[3.2.2]non-4-yl)-5-(2-chloro-5-trifluoromethylphenyl)-furan-2-yl-methanone;
(1,4-Diaza-bicyclo[3.2.2]non-4-yl)-5-(2-nitro-4-methylphenyl)-furan-2-yl-methanone;
(1,4-Diaza-bicyclo[3.2.2]non-4-yl)-5-(2-amino-4-methylphenyl)-furan-2-yl-methanone;
(1,4-Diaza-bicyclo[3.2.2]non-4-yl)-5-[4-(N,N-dimethylsulfonyl)aminophenyl]-furan-2-yl-methanone;
(1,4-Diaza-bicyclo[3.2.2]non-4-yl)-5-(4-formylaminophenyl)-furan-2-yl-methanone;
N-{4-[5-(1,4-Diaza-bicyclo[3.2.2]nonane-4-carbonyl)-furan-2-yl]-phenyl}-propionamide;
(1,4-Diaza-bicyclo[3.2.2]non-4-yl)-5-(3,5-dichlorophenoxy)-furan-2-yl-methanone;
(1,4-Diaza-bicyclo[3.2.2]non-4-yl)-5-[5-(trifluoromethyl-2-pyridyl)-thiomethyl]-furan-2-yl-methanone;
N-{4-[5-(1,4-Diaza-bicyclo[3.2.2]nonane-4-carbonyl)-furan-2-yl]-phenyl}-2,2,2-trifluoro-acetamide trifluoro acetic acid;
(1,4-Diaza-bicyclo[3.2.2]non-4-yl)-3-bromo-furan-2-yl-methanone;
(1,4-Diaza-bicyclo[3.2.2]non-4-yl)-5-phenylethynyl-furan-2-yl-methanone;
N-{4-[5-(1,4-Diaza-bicyclo[3.2.2]nonane-4-carbonyl)-furan-2-yl]-phenyl}-acrylamide;
N-{4-[5-(1,4-Diaza-bicyclo[3.2.2]nonane-4-carbonyl)-furan-2-yl]-phenyl}-benzamide;
(1,4-Diaza-bicyclo[3.2.2]non-4-yl)-5-[4-(N,N-diphenylsulfonylamino)phenyl]-furan-2-yl-methanone;
N-{4-[5-(1,4-Diaza-bicyclo[3.2.2]nonane-4-carbonyl)-furan-2-yl]-phenyl}-isobutyramide;
Cyclopropanecarboxylic acid {4-[5-(1,4-diaza-bicyclo[3.2.2]nonane-4-carbonyl)-furan-2-yl]-phenyl}-amide;
(1,4-Diaza-bicyclo[3.2.2]non-4-yl)-5-(4-aminophenyl)-furan-2-yl-methanone;
N-{4-[5-(1,4-Diaza-bicyclo[3.2.2]nonane 4-carbonyl)-furan-2-yl]-phenyl}-acrylamide N-oxide; or
N-{4-[5-(1,4-Diaza-bicyclo[3.2.2]nonane-4-carbonyl)-furan-2-yl]-phenyl}-acrylamide;
an enantiomers or a mixture of its enantiomers, or a pharmaceutically-acceptable addition salt thereof.

Any combination of two or more of the embodiments described herein is considered within the scope of the present invention.

Definition of Substituents

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention an alkoxy group designates an "alkyl-O—" group, wherein alkyl is as defined above. Examples of preferred alkoxy groups of the invention include methoxy and ethoxy.

In the context of this invention a cycloalkoxy group designates a "cycloalkyl-O—" group, wherein cycloalkyl is as defined above.

In the context of this invention a cyano-alkyl group designates an alkyl group substituted with CN, wherein alkyl is as defined above.

In the context of this invention halo represents fluoro, chloro, bromo or iodo, and haloalkyl group designates an alkyl group as defined herein, which alkyl group is substituted one or more times with halo. Thus a trihalomethyl group represents e.g. a trifluoromethyl group, a trichloromethyl group, and similar trihalo-substituted methyl groups. Preferred haloalkyl groups of the invention include trihalogenmethyl, preferably $CF_3$.

In the context of this invention a haloalkoxy group designates an alkoxy group as defined herein, which alkoxy group is substituted one or more times with halo. Preferred haloalkoxy groups of the invention include trihalogenmethoxy, preferably $CF_3O$—.

In the context of this invention an aryl group designates a monocyclic or polycyclic aromatic hydrocarbon group. Examples of preferred aryl groups of the invention include phenyl, indenyl, naphthyl, azulenyl, fluorenyl, and anthracenyl. The most preferred aryl group of the invention is phenyl.

In the context of this invention an aryloxy group designates an "aryl-O—" group, wherein aryl is as defined above. The most preferred aryloxy group of the invention is phenoxy.

In the context of this invention a heteroaryl group designates an aromatic mono- or polycyclic heterocyclic group, which holds one or more heteroatoms in its ring structure. Preferred heteroatoms include nitrogen (N), oxygen (O), and sulphur (S).

Preferred 5-6 membered heteroaryl groups of the invention include furanyl, in particular furan-2- or 3-yl; thienyl, in particular thien-2- or 3-yl; selenophenyl, in particular selenophen-2- or 3-yl; pyrrolyl (azolyl), in particular pyrrol-2- or 3-yl; oxazolyl, in particular oxazol-2, 4- or 5-yl; thiazolyl, in particular thiazol-2, 4- or 5-yl; imidazolyl, in particular imidazol-2- or 4-yl; pyrazolyl, in particular pyrazol-3- or 4-yl; isoxazolyl, in particular isoxazol-3, 4- or 5-yl; isothiazolyl, in particular isothiazol-3-, 4- or 5-yl; oxadiazolyl, in particular 1,2,3-oxadiazol-4- or 5-yl, or 1,3,4-oxadiazol-2-yl; triazolyl, in particular 1,2,3-triazol-4-yl or 1,2,4-triazol-3-yl; thiadiazolyl, in particular 1,2,3-thiadiazol-4- or 5-yl, or 1,3,4-thiadiazol-2-yl; pyridyl, in particular pyrid-2-, 3- or 4-yl; pyridazinyl, in particular pyridazin-3- or 4-yl; pyrimidinyl, in particular pyrimidin-2-, 4- or 5-yl; pyrazinyl, in particular pyrazin-2- or 3-yl; and triazinyl, in particular 1,2,4- or 1,3,5-triazinyl.

More preferred 5 membered heteroaryl groups of the invention include furanyl, in particular furan-2- or 3-yl; thienyl, in particular thien-2- or 3-yl; pyrrolyl (azolyl), in particular pyrrol-2- or 3-yl; oxazolyl, in particular oxazol-2, 4- or 5-yl; thiazolyl, in particular thiazol-2, 4- or 5-yl; isoxazolyl, in particular isoxazol-3, 4- or 5-yl; isothiazolyl, in particular isothiazol-3-, 4- or 5-yl; and thiadiazolyl, in particular 1,2,3-thiadiazol-4- or 5-yl, or 1,3,4-thiadiazol-2-yl.

Most preferred 5 membered heteroaryl groups of the invention include furanyl, in particular furan-2- or 3-yl; and thienyl, in particular thien-2- or 3-yl.

More preferred 6 membered heteroaryl groups of the invention include pyridyl, in particular pyrid-2-, 3- or 4-yl; and pyrazinyl, in particular pyrazin-2- or 3-yl.

In the context of this invention an aromatic bicyclic heterocyclic group designates a bicyclic heterocyclic group, which holds one or more heteroatoms in its ring structure. In the context of this invention the term "bicyclic heterocyclic group" includes benzo-fused five- and six-membered heterocyclic rings containing one or more heteroatoms. Preferred heteroatoms include nitrogen (N), oxygen (O), and sulphur (S).

Preferred bicyclic heteroaryl groups of the invention include indolizinyl, in particular indolizin-2-, 5- or 6-yl; indolyl, in particular indol-2-, 5- or 6-yl; isoindolyl, in particular isoindol-2-, 5- or 6-yl; benzo[b]furanyl, in particular benzofuran-2-, 5- or 6-yl; benzo[b]thienyl, in particular benzothien-2-, 5- or 6-yl; benzoimidazolyl, in particular benzoimidazol-2-, 5- or 6-yl; benzothiazolyl, in particular benzothiazol-5- or 6-yl; purinyl, in particular purin-2- or 8-yl; quinolinyl, in particular quinolin-2-, 3-, 6- or 7-yl; isoquinolinyl, in particular isoquinolin-3-, 6- or 7-yl; cinnolinyl, in particular cinnolin-6- or 7-yl; phthalazinyl, in particular phthalazin-6- or 7-yl; quinazolinyl, in particular quinazolin-2-, 6- or 7-yl; quinoxalinyl, in particular quinoxalin-2- or 6-yl; 1,8-naphthyridinyl, in particular 1,8-naphthyridin-2-, 3-, 6- or 7-yl; and pteridinyl, in particular pteridin-2-, 6- or 7-yl.

More preferred bicyclic heteroaryl groups of the invention include indolyl, in particular indol-2-, 5- or 6-yl; benzo[b]furanyl, in particular benzofuran-2-, 5- or 6-yl; benzo[b]thienyl, in particular benzothien-2-, 5- or 6-yl; benzoimidazolyl, in particular benzoimidazol-2-, 5- or 6-yl; and quinoxalinyl, in particular quinoxalin-2- or 6-yl.

Most preferred bicyclic heteroaryl groups of the invention include indolyl, in particular indol-2-, 5- or 6-yl; benzo[b]furanyl, in particular benzofuran-2-, 5- or 6-yl; benzo[b]thienyl, in particular benzothien-2-, 5- or 6-yl.

In the context of this invention a heteroaryloxy group designates a "heteroaryl-O—" group, wherein heteroaryl is as defined above.

Pharmaceutically Acceptable Salts

The diazabicyclic aryl derivative of the invention may be provided in any form suitable for the intended administraton. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzensulphonic acid, the benzoate derived from benzoic acid, the cinnamate derived from cinnamic acid, the citrate derived from citic acid, the embonate derived from embonic acid, the enantate derived from enanthic acid, the fumarate derived from fumaric acid, the glutamate derived from glutamic acid, the glycolate derived from glycolic add, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphtalene-2-sulphonic acid, the phthalate derived from phthalic acid, the salicylate derived from salicylic add, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Metal salts of a chemical compound of the invention include alkali metal salts, such as the sodium salt of a chemical compound of the invention containing a carboxy group.

Examples of pharmaceutically acceptable cationic salts of a chemical compound of the invention include, without limitation, the sodium, the potassium, the calcium, the magnesium, the zinc, the aluminium, the lithium, the choline, the lysine, and the ammonium salt, and the like, of a chemical compound of the invention containing an anionic group. Such cationic salts may be formed by procedures well known and described in the art.

In the context of this invention the "onium salts" of N-containing compounds are also contemplated as pharmaceutically acceptable salts (aza-onium salts). Preferred aza-onium salts include the alkyl-onium salts, in particular the methyl- and the ethyl-onium salts; the cycloalkyl-onium salts, in particular the cyclopropyl-onium salts; and the cycloalkylalkyl-onium salts, in particular the cyclopropyl-methyl-onium salts.

Particularly preferred onium salts of the invention include those created at the N' position according to the following Formula I'

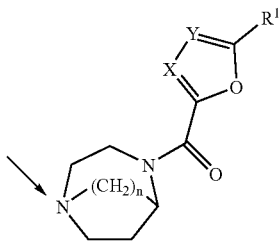

Steric Isomers

The chemical compounds of the present invention may exist in (+) and (−) forms as well as in racemic forms. The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l-(tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optical active starting materials.

Methods of Producing Diazabicyclic Aryl Derivatives

The diazabicyclic aryl derivative of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

The present invention is devoted to the provision novel ligands and modulators of the nicotinic receptors, which ligands and modulators are useful for the treatment of diseases or disorders related to the cholinergic receptors, and in particular the nicotinic acetylcholine receptor (nAChR). Preferred compounds of the invention show a pronounced nicotinic acetylcholine α7 receptor subtype selectivity.

The compounds of the present invention may in particular be agonists, partial agonists, antagonists and/or allosteric modulators of the nicotinic acetylcholine receptor.

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

The compounds of the invention may also be useful as diagnostic tools or monitoring agents in various diagnostic methods, and in particular for in vivo receptor imaging (neuroimaging), and they may be used in labelled or unlabelled form.

In a preferred embodiment the compounds of the invention are used for the treatment of diseases, disorders, or conditions relating to the central nervous system. Such diseases or disorders includes anxiety, cognitive disorders, learning deficit, memory deficits and dysfunction, Alzheimer's disease, attention deficit, attention deficit hyperactivity disorder (ADHD), Parkinson's disease, Huntington's disease, Amyotrophic Lateral Sclerosis, Gilles de la Tourette's syndrome, psychosis, depression, mania, manic depression, schizophrenia, obsessive compulsive disorders (OCD), panic disorders, eating disorders such as anorexia nervosa, bulimia and obesity, narcolepsy, nociception, AIDS-dementia, senile dementia, periferic neuropathy, autism, dyslexia, tardive dyskinesia, hyperkinesia, epilepsy, bulimia, post-traumatic syndrome, social phobia, sleeping disorders, pseudodementia, Ganser's syndrome, pre-menstrual syndrome, late luteal phase syndrome, chronic fatigue syndrome, mutism, trichotillomania, and jet-lag.

In a preferred embodiment diseases, disorders, or conditions relating to the central nervous system for which the compounds of the invention are used are cognitive disorders, psychosis, schizophrenia and/or depression.

In another preferred embodiment the compounds of the invention may be useful for the treatment of diseases, disorders, or conditions associated with smooth muscle contractions, including convulsive disorders, angina pectoris, premature labour, convulsions, diarrhoea, asthma, epilepsy, tardive dyskinesia, hyperkinesia, premature ejaculation, and erectile difficulty.

In yet another preferred embodiment the compounds of the invention may be useful for the treatment of endocrine disorders, such as thyrotoxicosis, pheochromocytoma, hypertension and arrhythmias.

In still another preferred embodiment the compounds of the invention may be useful for the treatment of neurodegenerative disorders, including transient anoxia and induced neuro-degeneraton.

In even another preferred embodiment the compounds of the invention may be useful for the treatment of inflammatory diseases, disorders, or conditions, including inflammatory skin disorders such as acne and rosacea, Chron's disease, inflammatory bowel disease, ulcerative colitis, and diarrhoea.

In still another preferred embodiment the compounds of the invention may be useful for the treatment of mild, moderate or even severe pain of acute, chronic or recurrent character, as well as pain caused by migraine, postoperative pain, and phantom limb pain. The pain may in particular be neuropathic pain, chronic headache, central pain, pain related to diabetic neuropathy, to post therapeutic neuralgia, or to peripheral nerve injury.

Finally the compounds of the invention may be useful for the treatment of withdrawal symptoms caused by termination of use of addictive substances. Such addictive substances include nicotine containing products such as tobacco, opioids such as heroin, cocaine and morphine, benzodiazepines and benzodiazepine-like drugs, and alcohol. Withdrawal from addictive substances is in general a traumatic experience characterised by anxiety and frustration, anger, anxiety, difficulties in concentrating, restlessness, decreased heart rate and increased appetite and weight gain.

In this context "treatment" covers treatment, prevention, prophylactics and alleviation of withdrawal symptoms and abstinence as well as treatment resulting in a voluntary diminished intake of the addictive substance.

In another aspect, the compounds of the invention are used as diagnostic agents, e.g. for the identification and localisation of nicotinic receptors in various tissues.

Pharmaceutical Compositions

In another aspect the invention provides novel pharmaceutical compositions comprising a therapeutically effective amount of the diazabicyclic aryl derivative of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the diazabicyclic aryl derivative of the invention, or a pharmaceutically acceptable salt or derivative thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be manufactured by the skilled person by use of standard methods and conventional techniques appropriate to the desired formulation. When desired, compositions adapted to give sustained release of the active ingredient may be employed.

The diazabicyclic aryl derivative of the invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

A therapeutically effective dose refers to that amount of active ingredient, which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions exhibiting large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

The diazabicyclic aryl derivatives of the present invention are valuable nicotinic receptor modulators, and therefore useful for the treatment of a range of ailments involving cholinergic dysfunction as well as a range of disorders responsive to the action of nAChR modulators.

In another aspect the invention provides a method for the treatment, prevention or alleviation of a disease or a disorder or a condition of a living animal body, including a human, which disease, disorder or condition is responsive to modulation of cholinergic receptors, and which method comprises administering to such a living animal body, including a human, in need thereof an effective amount of a diazabicyclic aryl derivative of the invention.

In the context of this invention the term "treatment" covers treatment, prevention, prophylaxis or alleviation, and the term "disease" covers illnesses, diseases, disorders and conditions related to the disease in question.

The preferred indications contemplated according to the invention are those stated above.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

A satisfactory result can, in certain instances, be obtained at a dosage as low as 0.005 mg/kg i.v. and 0.01 mg/kg p.o. The upper limit of the dosage range is about 10 mg/kg i.v. and 100 mg/kg p.o. Preferred ranges are from about 0.001 to about 1 mg/kg i.v. and from about 0.1 to about 10 mg/kg p.o.

EXAMPLES

The invention is further illustrated with reference to the following examples, which are not intended to be in any way limiting to the scope of the invention as claimed.

Example 1

Preparatory Example

All reactions involving air sensitive reagents or intermediates were performed under nitrogen and in anhydrous solvents.

1,4-Diazabicyclo[3.2.2]-nonan-3-one (Intermediate Compound)

32.33 g (200 mmol) of 3-Quinuclidinone hydrochloride was dissolved in 75 ml of water, and to the solution of hydroxylamine hydrochloride (16.4 g; 236 mmol) and $CH_3CO_2Na.3H_2O$ (80 g; 588 mmol) was added. The mixture was stirred at 70° C. for 1 hour. Then NaCl (10 g) was dissolved in the mixture and was cooled to 0° C. Separated crystals were filtered and carefully dried. The obtained crude 3-quinuclidone oxime (approx. 30 g) was used in the next step of the synthesis without further purification.

Polyphosphoric acid (180 g) of was heated to 100° C. and crude 3-quinuclidone oxime (30 g) was added portionwise. The reaction mixture was heated at 130° C. for 20 minutes. The mixture was cooled to room temperature, and 50 ml of water was added. The mass was carefully homogenised, the mixture was poured into of ice (100 g). The mixture was made alkaline (pH 12) by adding sodium hydroxide. The mixture was extracted with chloroform (2×400 ml). The extract was dried over sodium sulphate and the solvent was removed under reduced pressure.

Yield of the mixture of the products 1,4-diazabicyclo [3.2.2]nonan-3-one and 1,3-diazabicyclo[3.2.2]nonan-4-one was 19.02 g (68%). The mixture of isomers was crystallized from 80 ml of dioxane to yield 1,4-diazabicyclo[3.2.2]nonan-3-one (5.12 g; 18%). The solvent from filtrate was distilled off, flash chromatography (with acetone) of the residue gave of 1,3-diazabicyclo[3.2.2]nonan-4-one (8.91 g 32%).

1,4-Diazabicyclo[3.2.2]-nonane [J. Med. Chem. 1993 36 2311-2320](Intermediate Compound)

1,4-Diazabicyclo[3.2.2]nonan-3-one (5.12 g; 36 mmol) was dissolved in tetrahydrofuran (50 ml), litium aluminium hydride 2.28 g (60 mmol) was added to the solution and the reaction mixture was refluxed for 36 hours. After cooling the reaction mixture to mom temperature, water (2.3 ml) was added dropwise and the mixture was filtered. The solvent was removed from the filtrate by rotavapor at reduced pressure. The formed substance was distilled with Kugelrohr (0.5 mBar, 70° C.). Yield of the title compound 3.11 g (68%).

3-Bromo-2-furoic acid (Intermediate Compound)

To a mixture of 3-bromo furan (51.0 g; 0.347 mol) and THF (250 ml) was added lithiumdiisopropylamide (191 ml; 0.382 mol; 2M solution in heptane/THF/ethylbenzene) at −70° C. The mixture was stirred for 1 hour at −70° C. Solid carbondioxide (100.3 g; 2.28 mol) was added and the mixture was stirred until the carbondioxide was gone. Water (50 ml) was added followed by aqueous hydrochloric acid (380 ml; 2M). The tetrahydrofuran was evaporated. The mixture was extracted with diethylether (3×100 ml). The combined ether phase was extracted with aqueous sodium hydroxide (3×100 ml; 2M). The aqueous phase was cooled on ice and acidified with aqueous hydrochloric acid (100 ml; 10M). The mixture was extracted with ether (3×100 ml). The combined ether phase was evaporated. Yield 36 g (54%). Mp. 118.5° C.

Method A (1,4-Diaza-bicyclo[3.2.2]-non-4-yl)-furan-2-yl-methanone hydrochloric acid salt (Compound A1)

A mixture of 1,4-Diaza-bicyclo[3.2.2]nonane (0.50 g; 4.0 mmol), 2-furoyl chloride (0.52 mg; 4.0 mmol), diisopropylethylamine (1.02 g; 7.9 mmol) and 1,2-dimethoxyethane (25 ml) was stirred at room-temperatue over night. The product precipitated as hydrochloric acid salt and was filtered and washed with 1,2-dimethoxyethane (5 ml). Yield 0.84 g (82%). Mp. 279-283° C.

(1,4-Diaza-bicyclo[3.2.2]-non-4-yl)-5-bromo-furan-2-yl-methanone fumaric acid salt (Compound A2)

The title compound was prepared according to Method A, from 5-bromo-2-furoyl chloride (Method B) using no diisopropylethylamine. Aqueous sodium hydroxide (10 ml; 1M) was added. The mixture was extracted with dichloromethane (3×10 ml). Chromatography on silica gel with dichloromethane, methanol and conc. ammonia (89:10:1) gave the title compound. The corresponding salt was obtained by addition of a diethyl ether and methanol mixture (9:1) saturated with fumaric acid. Mp. 192.7-196.4° C.

(1,4-Diaza-bicyclo[3.2.2]-non-4-yl)-5-nitro-furan-2-yl-methanone hydrochloric acid salt (Compound A3)

The title compound was prepared according to Method A, from 5-nitro-2-furoyl chloride (Method B), using no diisopropylethylamine. Mp. 242.6-251.0° C.

(1,4-Diaza-bicyclo[3.2.2]-non-4-yl)-5-(4-nitrophenyl)-furan-2-yl-methanone hydrochloric acid salt (Compound A4)

The title compound was prepared according to Method A from 5-(4-nitrophenyl)-2-furoyl chloride (Method B), using no diisopropylethylamine. Mp. 298.2° C.

(1,4-Diaza-bicyclo[3.2.2]-non-4-yl)-5-(3-trifluoromethylphenyl)-furan-2-yl-methanone hydrochloric acid salt (Compound A5)

The title compound was prepared according to Method A from 5-(3-trifluoromethylphenyl)-2-furoyl chloride (Method B), using no diisopropylethylamine. Mp. 236.9° C.

(1,4-Diaza-bicyclo[3.2.2]-non-4-yl)-5-(4-chlorophenyl)-furan-2-yl-methanone hydrochloric acid salt (Compound A6)

The title compound was prepared according to Method A from 5-(4-chlorophenyl)-2-furoyl chloride (Method B), using no diisopropylethylamine. Mp. 272.5-274.7° C.

(1,4-Diaza-bicyclo[3.2.2]-non-4-yl)-5-(2-nitrophenyl)-furan-2-yl-methanone hydrochloric acid salt (Compound A7)

The title compound was prepared according to Method A from 5-(2-nitrophenyl)-2-furoyl chloride (Method B), using no diisopropylethylamine. Mp. 216.3-219.9° C.

(1,4-Diaza-bicyclo[3.2.2]-non-4-yl)-5-(3-nitrophenyl)-furan-2-yl-methanone hydrochloric acid salt (Compound A8)

The title compound was prepared according to Method A from 5-(3-nitrophenyl)-2-furoyl chloride (Method B), using no diisopropylethylamine. Mp. 224-230° C.

(1,4-Diaza-bicyclo[3.2.2]-non-4-yl)-8-methoxy-benzofuran-2-yl-methanone hydrochloric acid salt (Compound A9)

The title compound was prepared according to Method A from 8-methoxy-2-benzofuroyl chloride (Method B), using no diisopropylethylamine. Mp. 241-246° C.

(1,4-Diaza-bicyclo[3.2.2]-non-4-yl)-oxazolyl-5-yl-methanone hydrochloric acid salt (Compound A10)

The title compound was prepared according to Method A from 5-oxazoloyl chloride (Method B), using no diisopropylethylamine. Mp. >160° C. (decomp.).

(1,4-Diaza-bicyclo[3.2.2]-non-4-yl)-benzofuran-2-yl-methanone hydrochloric acid salt (Compound A11)

The title compound was prepared according to Method A from 2-benzofuroyl chloride (Method B), using no diisopropylethylamine. Mp. 264° C.

(1,4-Diaza-bicyclo[3.2.2]-non-4-yl)-3-methyl-furan-2-yl-methanone hydrochloric acid salt (Compound A12)

The title compound was prepared according to Method A from 3-methyl-2-furoyl chloride (Method B), using no diisopropylethylamine. Mp. 225.8-227.2° C.

(1,4-Diaza-bicyclo[3.2.2]-non-4-yl)-4,5-dibromo-furan-2-yl-methanone fumaric acid salt (Compound A13)

The title compound was prepared according to Method A from 4,5-dibromo-2-furoyl chloride (Method B), using no diisopropylethylamine. Mp. 250.9-254.3° C.

(1,4-Diaza-bicyclo[3.2.2]-non-4-yl)-5-(2-chloro-5-trifluoromethylphenyl)-furan-2-yl-methanone hydrochloric acid salt (Compound A14)

The title compound was prepared according to Method A from 5-(2-chloro-5-trifluoromethylphenyl)-2-furoyl chloride (Method B), using no diisopropylethylamine. Mp. 201° C.

(1,4-Diaza-bicyclo[3.2.2]-non-4-yl)-8-(2-nitro-4-methylphenyl)-furan-2-yl-methanone hydrochloric acid salt (Compound A15)

The title compound was prepared according to Method A from 5-(2-nitro-4-methylphenyl)-2-furoyl chloride (Method B), using no diisopropylethylamine. Mp. 199° C.

(1,4-Diaza-bicyclo[3.2.2]-non-4-yl)-3-methyl-benzofuran-2-yl-methanone hydrochloric acid salt (Compound A16)

The title compound was prepared according to Method A from 3-methyl-2-benzofuroyl chloride (Method B), using no diisopropylethylamine. Mp. 260-276° C.

(1,4-Diaza-bicyclo[3.2.2]-non-4-yl)-5-phenyl-1,3,4-oxadiazol-2-yl-methanone hydrochloric acid salt (Compound A17)

The title compound was prepared according to Method A from 5-methyl-1,3,4-oxadiazol-2-carbonyl-chloride chloride, using no diisopropylethylamine. Mp. 280-290° C.

(1,4-Diaza-bicyclo[3.2.2]non-4-yl)-5-(3,5-dichlorophenoxy)-furan-2-yl-methanone hydrochloric acid salt (Compound A18)

The title compound was prepared according to Method A from 5-(3,5-dichlorophenoxy)-furan-2-carbonyl chloride, using no diisopropylethylamine. Mp. 124° C.

(1,4-Diaza-bicyclo[3.2.2]-non-4-yl)-5-[5-(trifluoromethyl-2-pyridyl)-thiomethyl]-furan-2-yl-methanone hydrochloric acid salt (Compound A19)

The title compound was prepared according to Method A from 5-[5-(trifluoromethyl-2-pyridyl)-thiomethyl]-furan-2-carbonyl chloride, using no diisopropylethylamine. Mp. 176° C.

(1,4-Diaza-bicyclo[3.2.2]non-4-yl)-3-bromo-furan-2-yl-methanone fumaric acid salt (Compound A20)

The title compound was prepared according to Method A, from 3-bromo-2-furoyl chloride (Method B from 3-bromo-2-furoic acid) using no diisopropylethylamine. Mp. 157.4-159.9° C.

(1,4-Diaza-bicyclo[3.2.2]non-4-yl)-5-phenylethynyl-furan-2-yl-methanone fumaric acid salt (Compound A21)

The title compound was prepared according to Method A, from 5-(2-phenylethynyl)-2-furanoic acid chloride. Mp. 166.3-168.3° C.

Method B

3-Bromo-2-furoic acid (Intermediate Compound)

To a mixture of 3-bromo furan (51.0 g; 0.347 mol) and THF (250 ml) was added lithiumdiisopropylamide (191 ml; 0.382 mol; 2 M solution in heptane/THF/ethylbenzene) at −70° C. The mixture was stirred for 1 hour at −70° C. Solid carbondioxide (100.3 g; 2.28 mol) was added and the mixture was stirred until the carbondioxide was gone. Water (50 ml) was addded followed by aqueous hydrochloric acid (380 ml; 2M). The tetrahydrofuran was evaporated. The mixture was extracted with diethylether (3×100 ml). The combined ether phase was extracted with aqueous sodium hydroxide (3×100 ml; 2M). The aqueous phase was cooled on ice and acidified with aqueous hydrochloric acid (100 ml; 10M). The mixture was extracted with ether (3×100 ml). The combined ether phase was evaporated. Yield 36 g (54%). Mp. 118.5° C.

5-(4-nitrophenyl)-2-furoyl chloride (Intermediate Compound)

The title compound was prepared by stirring a mixture of 5-(4-nitrophenyl)-2-furoic acid (1.0 g; 4.3 mmol) and thionyl chloride (10 ml) at reflux for 2 hours. The mixture was evaporated and co-evaporated with anhydrous toluene. The acid chloride was used without further purification.

Method C

(1,4-Diaza-bicyclo[3.2.2]-non-4-yl)-5-(4-aminophenyl)-furan-2-yl-methanone fumaric acid salt (Compound C1)

A mixture of (1,4-diaza-bicyclo[3.2.2]non-4-yl)-5-(4-nitrophenyl)-furan-2-yl-methanone (0.70 g; 1.9 mmol), palladium on carbon (400 mg; 5%) and ethanol (30 ml) was stirred under hydrogen for 24 hours. The mixture was filtered through celite and evaporated. Yield 0.44 g (74%). The corresponding salt was obtained by addition of a diethyl ether and methanol mixture (9:1) saturated with fumaric acid. Mp. 227.8° C.

(1,4-Diaza-bicyclo[3.2.2]-non-4-yl)-5-(2-aminophenyl)-furan-2-yl-methanone fumaric acid salt (Compound C2)

The title compound was prepared according to Method C from (1,4-diaza-bicyclo[3.2.2]non-4-yl)-5-(2-nitrophenyl)-furan-2-yl-methanone. Mp. 201.1-207.3° C.

(1,4-Diaza-bicyclo[3.2.2]-non-4-yl)-5-(3-aminophenyl)-furan-2-yl-methanone fumaric acid salt (Compound C3)

The title compound was prepared according to Method C from (1,4-diaza-bicyclo[3.2.2]non-4-yl)-5-(3-nitrophenyl)-furan-2-yl-methanone. Mp. 184.9-188.2° C.

(1,4-Diaza-bicyclo[3.2.2]non-4-yl)-5-(2-amino-4-methylphenyl)-furan-2-yl-methanone fumaric acid salt (Compound C4)

The title compound was prepared according to Method C from (1,4-diaza-bicyclo[3.2.2]non-4-yl)-5-(2-nitro-4-methylphenyl)-furan-2-yl-methanone. Mp. 179° C.

Method D

(1,4-Diaza-bicyclo[3.2.2]-non-4-yl)-5-(4-acetylaminophenyl)-furan-2-yl-methanone (Compound D1)

Acetic acid anhydride (133 mg; 1.3 mmol) solved in dichloromethane (2 ml) was added dropwise to a mixture of (1,4-diaza-bicyclo[3.2.2]non-4-yl)-5-(4-aminophenyl)-furan-2-yl-methanone and dichloromethane (10 ml) at room temperature. The mixture was allowed to stir for 4 hours. Aqueous sodium hydroxide (20 ml; 1M) was added followed by extraction with dichloromethane (3×20 ml). The crude mixture was purified by silica gel chromatography, using a mixture of dichloromethane:methanol (4:1) and 2% methanol as eluent. The product was isolated as the free base. Mp. 113° C. (decomp.).

(1,4-Diaza-bicyclo[3.2.2]-non-4-yl)-5-(2-acetylaminophenyl)-furan-2-yl-methanone fumaric acid salt (Compound D2)

The title compound was prepared according to Method D from (1,4-diaza-bicyclo[3.2.2]non-4-yl)-5-(2-aminophenyl)-furan-2-yl-methanone. The corresponding salt was obtained by addition of a diethyl ether and methanol mixture (9:1) saturated with fumaric acid. Mp. 178.9-185.0° C.

(1,4-Diaza-bicyclo[3.2.2]-non-4-yl)-5-(3-acetylaminophenyl)-furan-2-yl-methanone fumaric acid salt (Compound D3)

The title compound was prepared according to Method D from (1,4-diaza-bicyclo[3.2.2]non-4-yl)-(3-aminophenyl)-furan-2-yl-methanone. The corresponding salt was obtained by addition of a diethyl ether and methanol mixture (9:1) saturated with fumaric acid. Mp. 216° C.

N-{4-[5-(1,4-Diaza-bicyclo[3.2.2]-nonane-4-carbonyl)-furan-2-yl]-phenyl}-propionamide free base (Compound D4)

The title compound was prepared according to Method D from (1,4-diaza-bicyclo[3.2.2]non-4-yl)-5-(4-aminophenyl)-furan-2-yl-methanone. Mp. 264° C.

N-{4-[5-(1,4-Diaza-bicyclo[3.2.2]-nonane-4-carbonyl)-furan-2-yl]-phenyl}2,2,2-trifluoro-acetamide trifluoro acetic acid salt (Compound D5)

The title compound was prepared according to Method D from (1,4-diaza-bicyclo[3.2.2]non-4-yl)-5-(4-aminophenyl)-furan-2-yl-methanone and trifluoroacetic anhydride. Mp. 219° C.

N-{4-[5-(1,4-Diaza-bicyclo[3.2.2]-nonane-4-carbonyl)-furan-2-yl]-phenyl}-isobutyramide fumaric acid salt (Compound D6)

The title compound was prepared according to Method D from (1,4-diaza-bicyclo[3.2.2]non-4-yl)-5-(4-aminophenyl)-furan-2-yl-methanone and isobutyric anhydride. Mp. 223° C.

Method E

(1,4-Diaza-bicyclo[3.2.2]-non-4-yl)-5-[4-(N,N-dimethylsulfonyl)aminophenyl]-furan-2-yl-methanone free base (Compound E1)

A mixture of (1,4-diaza-bicyclo[3.2.2]non-4-yl)-5-(4-aminophenyl)-furan-2-yl-methanone (0.5 g; 1.6 mmol) and dichloromethane (5 ml), methanesulfonyl chloride (2.12 g; 18.4 mmol) and dichloromethane (5 ml) was stirred at room temperature for 15 hours. Aqueous sodium hydroxide (5 ml; 1M) was added followed by extraction with dichloromethane (3×5 ml). The crude mixture was purified by silica gel chromatography, using a mixture of dichloromethane:methanol (9:1) and 1% methanol as eluent. The product was isolated as the free base. Yield 20 mg (3%). Mp. 189° C.

N-{4-[5-(1,4-Diaza-bicyclo[3.2.2]-nonane-4-carbonyl)-furan-2-yl]-phenyl}-acrylamide fumaric acid salt (Compound E2)

The title compound was prepared according to Method E from (1,4-diaza-bicyclo[3.2.2]non-4-yl)-5-(4-aminophenyl)-furan-2-yl-methanone and acryloyl chloride (1.6 eq.). Mp. 220° C.

N-{4-[5-(1,4-Diaza-bicyclo[3.2.2]nonane-4-carbonyl)-furan-2-yl]-phenyl}-benzamide fumaric acid salt (Compound E3)

The title compound was prepared according to Method E from (1,4-diaza-bicyclo[3.2.2]non-4-yl)-(4-aminophenyl-4-furan-2-yl-methanone, diisopropylethylamine (2 eq.) and benzoyl chloride (1.5 eq.). Mp. 254° C.

(1,4-Diaza-bicylo[3.2.2]non-4-yl)-5-[4-(N,N-diphenylsulfonylamino)phenyl]-furan-2-yl-methanone fumaric acid salt (Compound E4)

The title compound was prepared according to Method E from (1,4-diaza-bicyclo[3.2.2]non-4-yl)-5-(4-aminophenyl)-furan-2-yl-methanone, diisopropylethylamine (2 eq.) and benzenesulfonyl chloride (1.5 eq.). Mp. 201-203° C.

Cyclopropanecarboxylic acid {4-[5-(1,4-diaza-bicyclo[3.2.2]-nonane-4-carbonyl)-furan-2-yl]-phenyl}-amide fumaric acid salt (Compound E5)

The title compound was prepared according to Method E from (1,4-diaza-bicyclo[3.2.2]non-4-yl)-5-(4-aminophenyl)-furan-2-yl-methanone, cyclopropanecarbonyl chloride. Mp. 254° C.

Method F

(1,4-Diaza-bicyclo[3.2.2]-non-4-yl)-5-(4-formylaminophenyl)-furan-2-yl-methanone (Compound F1)

A mixture of (1,4-diaza-bicyclo[3.2.2]non-4-yl)-5-(4-aminophenyl)-furan-2-yl-methanone (0.50 g; 1.6 mmol) and ethylformate (30 ml) was stirred at reflux for 9 days. The mixture was evaporated. Aqueous sodium hydroxide (20 ml; 1M) was added followed by extraction with dichloromethane (3×20 ml). The crude mixture was purified by silica gel chromatography, using a mixture of dichloromethane:methanol (9:1) and 1% methanol as eluent. The product was isolated as the free base. Yield 0.29 g (53%). Mp. 236° C.

Method G

(1,4-Diaza-bicyclo[3.2.2]-non-4-yl)-5-(4-aminophenyl)-furan-2-yl-methanone chloromethylium chloride salt (Compound G1)

Ethylisothiocyanate (182 mg; 2.09 mmol) solved in dichloromethane (20 ml) was added dropwise to a mixture of (1,4-diaza-bicyclo[3.2.2]non-4-yl)-5-(4-aminophenyl)-furan-2-yl-methanone and dichloromethane (10 ml) at 5° C. The mixture was allowed to stir for 4 hours at 5° C. and 11 hours at room temperature. The solvent volume was reduced to a third and the solid product was isolated by filtration. Mp. >300° C.

Method H

N-{4-[5-(1,4-Diaza-bicyclo[3.2.2]nonane-4-carbonyl)-furan-2-yl]-phenyl}-acrylamide methyllum iodide (Compound H1)

A mixture of N-{4-[5-(1,4-Diaza-bicyclo[3.2.2]nonane-4-carbonyl)-furan-2-yl]-phenyl}-acrylamide (175 mg; 0.479 mmol) and dichloromethane (10 ml) was stirred at −70° C. Iodomethane (68 mg (0.479 mmol) solved in dichloromethane (5 ml) was added. The mixture was allowed to stir at −70° C. for 1 hour. The mixture was allowed to reach room temperature and was evaporated and triturated with diethyl-ether. Yield 0.15 g (62%). Mp. 230-246° C.

Method I

N-{4-[5-(1,4-Diaza-bicyclo[3.2.2]nonane-4-carbonyl)-furan-2-yl]-phenyl}-acrylamide N-oxide (Compound I1)

A mixture of N-{4-[5-(1,4-Diaza-bicyclo[3.2.2]nonane-4-carbonyl)-furan-2-yl]-phenyl}-acrylamide (175 mg; 0.479 mmol), m-chloroperoxybenzoic acid (165 mg; 0.958 mmol) and dichloromethane (5 ml) was stirred at room-temperature for 15 hours. The crude mixture was evaporated. Chromatography on silica gel with dichloromethane, methanol and conc. ammonia (89:10:1) gave the title compound. Yield 180 mg (99%). Mp. 162° C.

Example 2

In Vitro Inhibition of $^3$H-α-Bungarotoxine Binding in Rat Brain

In this example the affinity of the compounds of the invention for binding to $α_7$-subtype of nicotinic receptors is determined.

α-Bungarotoxine is a peptide isolated from the venom of the Elapidae snake *Bungarus multicinctus*. It has high affinity for neuronal and neuromuscular nicotinic receptors, where it acts as a potent antagonist. $^3$H-α-Bungarotoxine labels nicotinic acetylcholine receptors formed by the $α_7$ subunit isoform found in brain and the $α_1$ isoform in the neuromuscular junction.

Tissue Preparation

Preparations are performed at 0-4° C. Cerebral cortices from male Wistar rats (150-250 g) are homogenised for 10 seconds in 15 ml of 20 mM Hepes buffer containing 118 mM NaCl, 4.8 mM KCl, 1.2 mM MgSO$_4$ and 2.5 mM CaCl$_2$ (pH 7.5) using an Ultra-Turrax homogeniser. The tissue suspension is subjected to centrifugation at 27,000×g for 10 minutes. The supernatant is discarded and the pellet is washed twice by centrifugation at 27,000×g for 10 minutes in 20 ml of fresh buffer, and the final pellet is then re-suspended in fresh buffer containing 0.01% BSA (35 ml per g of original tissue) and used for binding assays.

Assay

Aliquots of 500 μl of homogenate are added to 25 μl of test solution and 25 μl of $^3$H-α-bungarotoxine (2 nM, final concentration) and mixed and incubated for 2 hours at 37° C. Non-specific binding is determined using (−)-nicotine (1 mM, final concentration). After incubation, the samples are added 5 ml of ice-cold Hepes buffer containing 0.05% PEI and poured directly onto Whatman GF/C glass fibre filters (pre-soaked in 0.1% PEI for at least 6 hours) under suction, and immediately washed with 2×5 ml ice-cold buffer.

The amount of radioactivity on the filters is determined by conventional liquid scintillation counting. Specific binding is total binding minus non-specific binding.

The test value is given as an IC$_{50}$ (the concentration of the test substance which inhibits the specific binding of $^3$H-α-bungarotoxin by 50%).

The results of these experiments are presented in Table 1 below.

TABLE 1

Inhibition of $^3$H-α-Bungarotoxine Binding

| Compound No. | IC$_{50}$ (μM) |
|---|---|
| A1 | 0.54 |
| A5 | 0.051 |
| C3 | 0.080 |
| F1 | 0.017 |

The invention claimed is:
1. A diazabicyclic aryl compound represented by Formula I

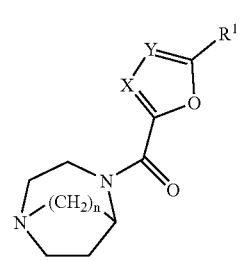

any of its enantiomers or any mixture of its enantiomers, or a pharmaceutically acceptable addition salt thereof, wherein
n is 2;
X and Y, independently of each other, represents CR$^2$ or N;
R$^1$ represents alkyl, cycloalkyl, cycloalkyl-alkyl, alkoxy, CF$_3$, OCF3, CN, nitro, 2-nitro-phenyl, 3-nitro-phenyl, 4-nitro-phenyl, 3-trifluoromethyl-phenyl, 4-trifluoromethyl-phenyl, 2-halo-5-trifluoromethyl-phenyl, 2-amino-phenyl, 3-amino-phenyl, N-4-formylaminophenyl, N-2-acetylamino-phenyl, N-3-acetylaminophenyl, or N-4-acetylamino-phenyl; and
R$^2$ represents hydrogen, alkyl or halo.
2. The diazabicyclic aryl compound of claim 1, represented by Formula II

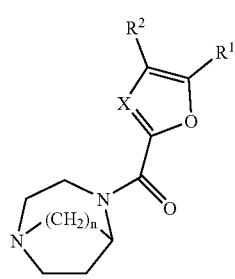

any of its enantiomers or any mixture of its enantiomers, or a pharmaceutically acceptable addition salt thereof, wherein
n is 2;
X represents CR$^4$ or N
R$^1$ represents alkyl, cycloalkyl, cycloalkyl-alkyl, alkoxy, CF$_3$, OCF$_3$, CN, nitro, 2-nitro-phenyl, 3-nitro-phenyl, 4-nitro-phenyl, 3-trifluoromethyl-phenyl, 4-trifluoromethyl-phenyl, 2-halo-5-trifluoromethyl-phenyl, 2-amino-phenyl, 3-amino-phenyl, N-4-formylaminophenyl, N-2-acetylamino-phenyl, N-3-acetylaminophenyl, or N-4-acetylamino-phenyl;

$R^2$ represents hydrogen or halo; and $R^4$ represents hydrogen, alkyl or halo.

3. The diazabicyclic aryl compound of claim 1, which is (1,4-Diaza-bicyclo[3.2.2]non-4-yl)-5-nitro-furan-2-yl-methanone;

(1,4-Diaza-bicyclo[3.2.2]non-4-yl)-5-(4-nitrophenyl)-furan-2-yl-methanone;

(1,4-Diaza-bicyclo[3.2.2]non-4-yl)-5-(3-trifluoromethylphenyl)-furan-2-yl-methanone;

(1,4-Diaza-bicyclo[3.2.2]non-4-yl)-5-(2-nitrophenyl)-furan-2-yl-methanone;

(1,4-Diaza-bicyclo[3.2.2]non-4-yl)-5-(3-nitrophenyl)-furan-2-yl-methanone;

(1,4-Diaza-bicyclo[3.2.2]non-4-yl)-5-(4-acetylaminophenyl)-furan-2-yl-methanone;

(1,4-Diaza-bicyclo[3.2.2]non-4-yl)-5-(2-aminophenyl)-furan-2-yl-methanone;

(1,4-Diaza-bicyclo[3.2.2]non-4-yl)-5-(3-aminophenyl)-furan-2-yl-methanone;

(1,4-Diaza-bicyclo[3.2.2]non-4-yl)-5-(2-acetylaminophenyl)-furan-2-yl-methanone (1,4-Diaza-bicyclo[3.2.2]non-4-yl)-5-(3-acetylaminophenyl)-furan-2-yl-methanone; or any enantiomers or a mixture of its enantiomers, or a pharmaceutically acceptable addition salt thereof.

4. A pharmaceutical composition comprising a therapeutically effective amount of a diazabicyclic aryl compound of claim 1, any of its enantiomers or any mixture of its enantiomers or a pharmaceutically acceptable addition salt thereof together with at least one pharmaceutically acceptable carrier or diluent.

* * * * *